(12) United States Patent
Hayashi et al.

(10) Patent No.: US 6,425,665 B2
(45) Date of Patent: Jul. 30, 2002

(54) VISUAL ACUITY EXAMINATION APPARATUS

(75) Inventors: Akihiro Hayashi, Toyokawa; Yuichiro Kanazawa, Okazaki; Noritsugu Nozawa, Toyokawa, all of (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/817,083

(22) Filed: Mar. 27, 2001

(30) Foreign Application Priority Data

Mar. 31, 2000 (JP) ........................................ 2000-096087
Mar. 31, 2000 (JP) ........................................ 2000-096090

(51) Int. Cl.[7] ................................................ A61B 3/02
(52) U.S. Cl. .................................................... 351/239
(58) Field of Search ................................ 351/237, 238, 351/239, 240, 243, 244, 245, 246

(56) References Cited

U.S. PATENT DOCUMENTS 5,129,720 A * 7/1992 Jovicevic .................... 351/243
6,244,713 B1 * 6/2001 Hayashi ..................... 351/243

* cited by examiner

Primary Examiner—George Manuel
(74) Attorney, Agent, or Firm—Oliff & Berridge, PLC

(57) ABSTRACT

A visual acuity examination apparatus for examining a visual acuity of an examinee by presenting an optotype to the examinee includes an optotype presenting unit which selectively presents at least one of a plurality of comparison optotypes expressed in geometrical series, the optotypes being provided to be plural in number for each visual acuity value, an input unit with which a distinction answer of the examinee with respect to the presented optotype is input, a storage unit in which an examination program which sequentially determines an optotype to be next presented based on whether the distinction answer with respect to the presented optotype is right or wrong is stored, a control unit which controls the optotype presenting unit in accordance with the examination program, and a processing unit which determines a visual acuity value of the examinee from a percentage of right answers in the distinction answers with respect to an optotype for a visual acuity value.

10 Claims, 12 Drawing Sheets

VISUAL ACUITY EXAMINATION APPARATUS

BACKGROUND OF THE INVENTION

1. Field of the Invention

The present invention relates to a visual acuity examination apparatus for examining the visual acuity of an examinee, or an eye of the examinee, by presenting optotypes to the examinee.

2. Description of Related Art

There have been known visual acuity examination apparatuses for estimating the visual acuity of an examinee by sequentially presenting a plurality of optotypes for different visual acuity values (visual acuity levels or scales) to the examinee, or an eye of the examinee, and determining the visual acuity of the examinee based on whether the examinee could see (distinguish) or not the presented optotypes. Heretofore, the visual acuity examination apparatus of this type would generally perform a visual acuity examination by the use of optotypes expressed in decimal values for visual acuity.

However, the optotypes expressed in the decimal visual acuity values differ in size difference according to visual acuity values, and therefore accurate estimation could not be executed. To be more specific, in the decimal visual acuity values, the improvement in visual acuity from 0.2 to 0.3 and the improvement from 0.9 to 1.0 are both considered as the improvement of one level of visual acuity. However, if expressing in visual angle, the increase from 0.2 to 0.3 corresponds to 1.5 times the visual angle, while the increase from 0.9 to 1.0 corresponds to about 1.1 (1.0/0.9) times. Therefore, it would be difficult to make the same estimation in the above cases.

In judgement of the visual acuity, if five optotypes for the same visual acuity value are used, the maximum value among the visual acuity values of the optotypes to which three or more right answers are given (i.e., the largest value in decimal visual acuity values) is directly regarded as the visual acuity value of the examinee (the examinee's eye). Consequently, the estimation would be rough and insufficient for the ophthalmologists and the like to confirm treatment results and correction results.

SUMMARY OF THE INVENTION

The present invention has been made in view of the above circumstances and has an object to overcome the above problems and to provide a visual acuity examination apparatus capable of easily and simply obtaining and estimating the visual acuity of an examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual acuity examination apparatus for examining a visual acuity of an examinee by presenting an optotype to the examinee, the apparatus including: an optotype presenting unit which selectively presents at least one of a plurality of comparison optotypes expressed in geometrical series, the optotypes being provided to be plural in number for each visual acuity value; an input unit with which a distinction answer of the examinee with respect to the presented optotype is input; a storage unit in which an examination program which sequentially determines an optotype to be next presented based on whether the distinction answer with respect to the presented optotype is right or wrong is stored; a control unit which controls the optotype presenting unit in accordance with the examination program; and a processing unit which determines a visual acuity value of the examinee from a percentage of right answers in the distinction answers with respect to an optotype for a visual acuity value.

According to another aspect of the present invention, there is provided a visual acuity examination apparatus which switches and displays an optotype in a screen, the apparatus including: an optotype disc plate on which a plurality of charts each provided with one optotype or a plurality of optotypes are formed in a circle, the plurality of optotypes being configured in one line or three line in the chart; a mask disk plate on which a plurality of masks for presenting one optotype or at least a part of the optotypes formed on the chart; and a rotating unit which individually rotates the optotype disc plate and the mask disc plate, thereby to selectively present the optotype.

According to another aspect of the present invention, there is provided a visual acuity examination apparatus for examining a visual acuity of an examinee by presenting an optotype to the examinee, the apparatus including: an optotype presenting unit which selectively presents at least one of a plurality of comparison optotypes expressed in geometrical series, the optotypes being provided to be plural in number for each visual acuity value; an input unit with which a distinction answer of the examinee with respect to the presented optotype is input; a storage unit in which an examination program which sequentially determines an optotype to be next presented based on whether the distinction answer with respect to the presented optotype is right or wrong is stored; and a control unit which controls the optotype presenting unit in accordance with the examination program.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
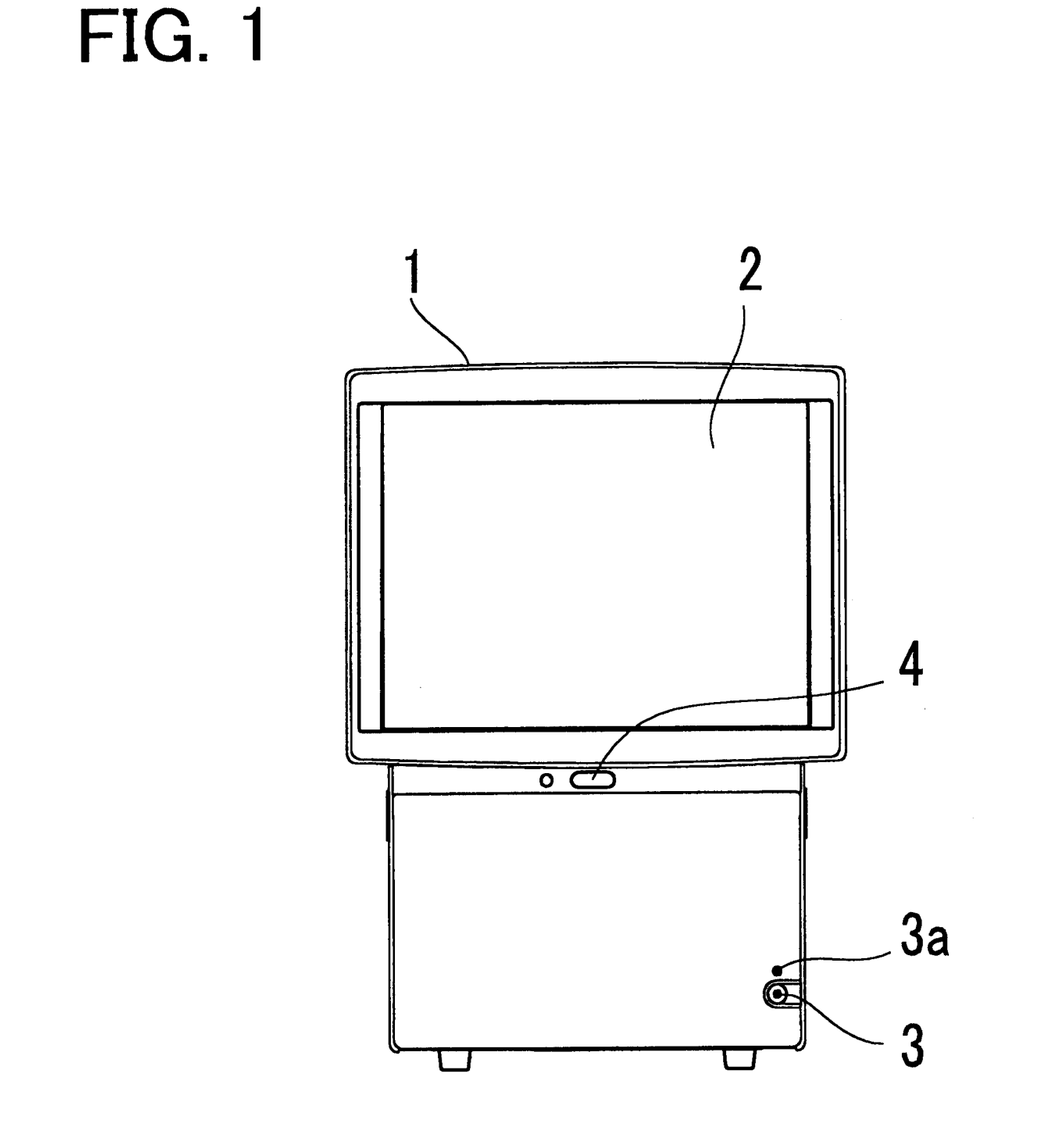
FIG. 1 is a schematic front view of a main unit of a visual acuity examination apparatus in an embodiment according to the present invention.

A detailed description of a preferred embodiment of a visual acuity examination apparatus embodying the present invention will now be given referring to the accompanying drawings. FIG. 1 is a schematic front view of the visual acuity examination apparatus in the embodiment.

Numeral 1 is a main unit provided, at its front upper portion, with a window 2 made of a glass plate on which an antireflective film is provided. An examinee is allowed to view through this window 2 optotypes which should be presented in a center of the main unit 1. This window 2 may be made of a filter instead of the glass plate. The interior of the main unit 1 is painted in black color so that the examinee can hardly look the interior structure of the main unit 1.

Numeral 3 is a power switch, and 3a is an indication lamp for informing that the power switch 3 has been turned on. Numeral 4 is a window for transmission and receipt of optical signals with respect to a wireless remote control unit 40 which will be mentioned later.

Figure 2:
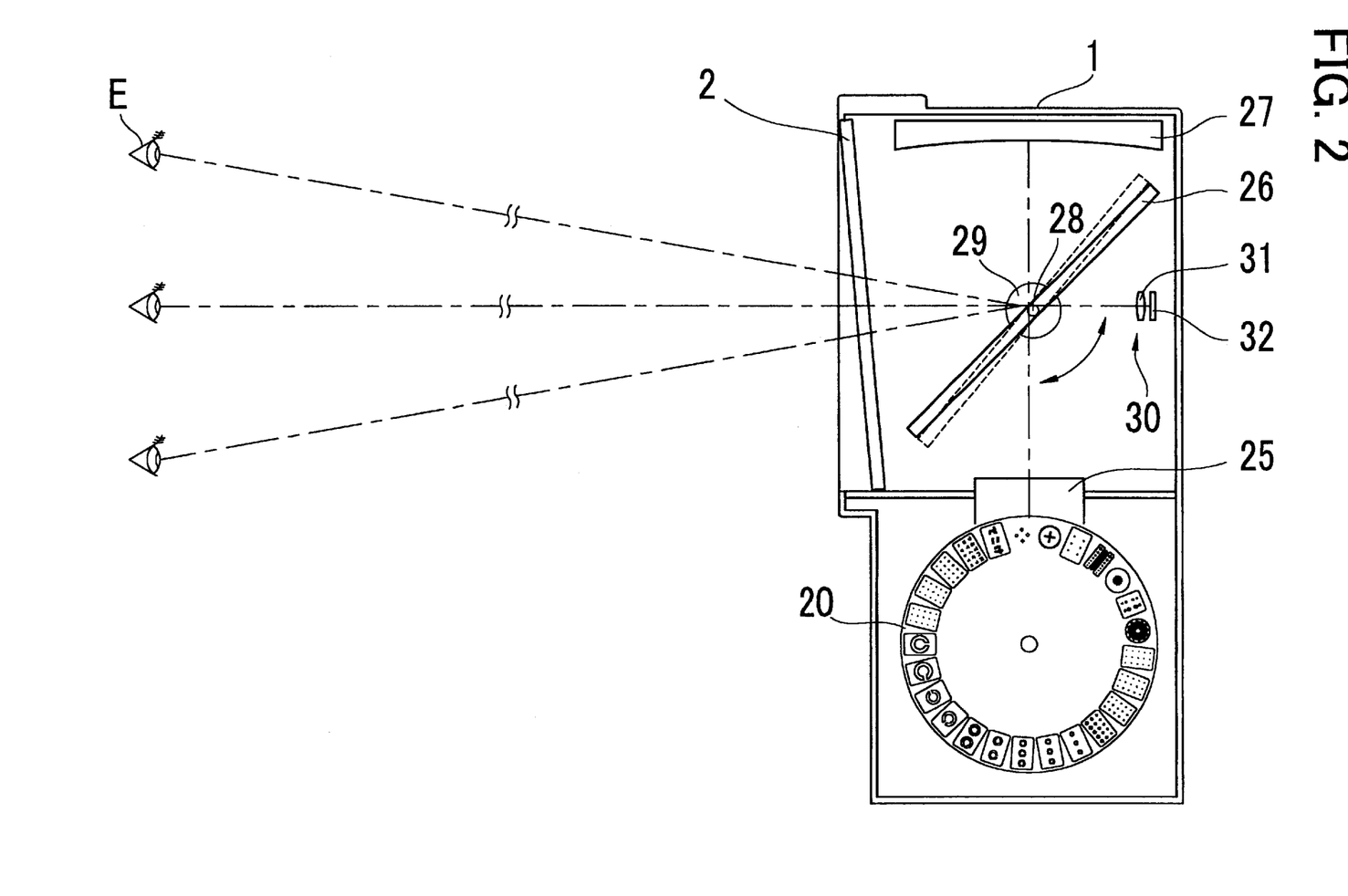
FIG. 2 is a schematic view of an optical system disposed in the main unit seen from side.
Figure 3:
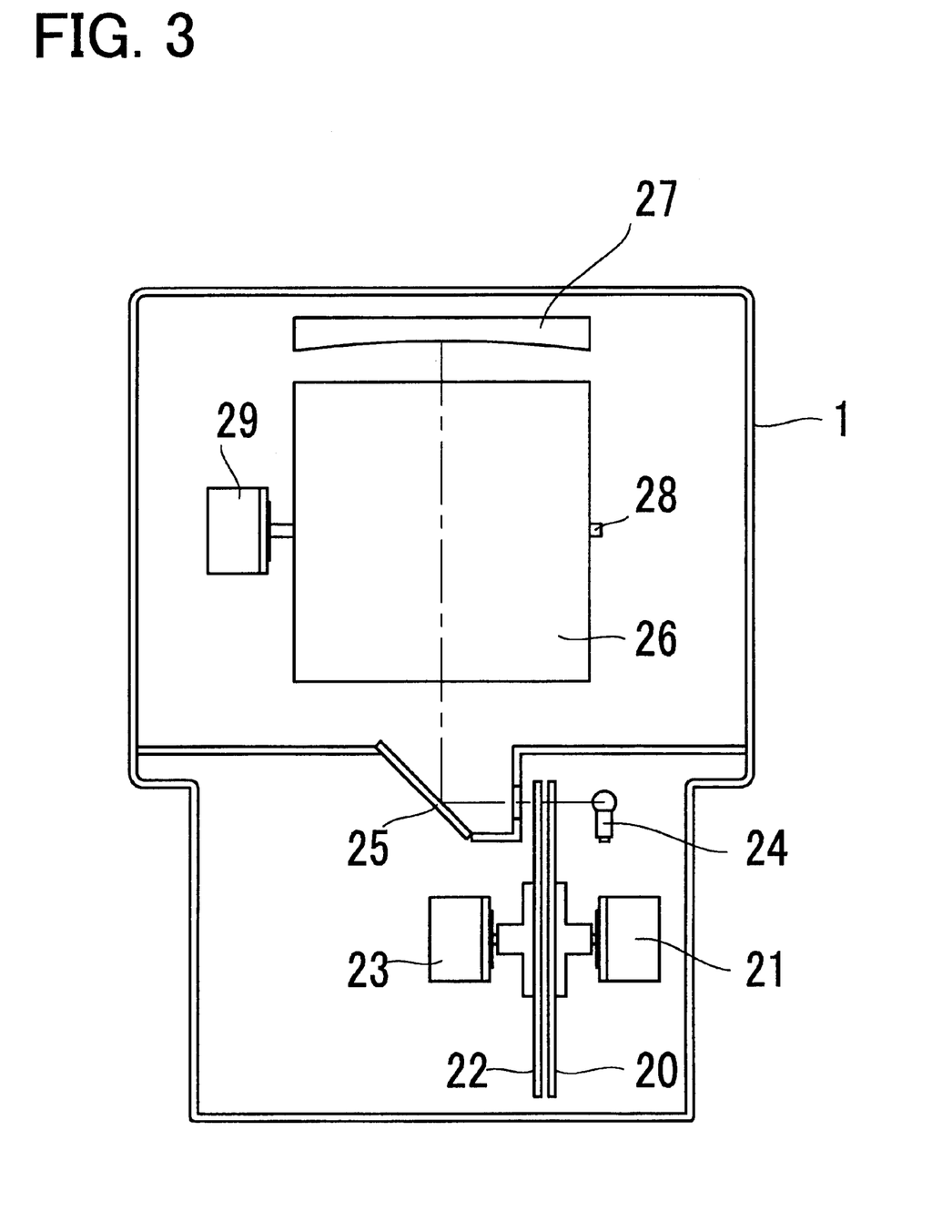
FIG. 3 is a schematic view of the optical system disposed in the main unit seen from front.

Next, an optical system disposed in the main unit 1 is explained with reference to FIGS. 2 and 3. FIG. 2 is a schematic right side view of the main unit 1 with the optical system seen therethrough. FIG. 3 is a schematic front view of the main unit 1 with the optical system seen therethrough.

An alphabet E denotes an eye of an examinee. Numeral 20 is an optotype disc plate made of glass. On this disc plate 20, many optotypes for visual acuity examination such as optotypes for various visual acuity values and others are formed in a circle by chrome evaporation and the like. The optotype disc plate 20 is rotated by a motor 21 to change optotypes (charts) to be presented to the examinee. Numeral 22 is a mask disc plate for partially masking the optotypes. This mask disc plate 22 is rotated by a motor 23 to cover a desired part of the disc plate 20. The details of the optotype disc plate 20 and the mask disc plate 22 will be described later.

Numeral 24 is an illumination lamp for illuminating the optotypes (charts) provided on the optotype disc plate 20; 25 is a mirror; 26 is a beam splitter; and 27 is a concave mirror. The concave mirror 27 in the present embodiment is designed to have a focal distance so that an optical distance between the optotype and the examinee's eye E is adjusted to an examination distance of 5 m when the distance between the eye E and the window 2 is 0.9 m.

Luminous flux of the optotype illuminated by the illumination lamp 24 is reflected upward by the mirror 25, permitted to transmit through the beam splitter 26, and reflected by the concave mirror 27. The optotype luminous flux reflected by the mirror 27 is then reflected by the beam splitter 26 toward the eye E through the window 2. Since the beam splitter 26 is fixed to a rotating shaft 28, an inclination angle of the beam splitter 26 is changed in accordance with the rotation of the shaft 28 caused by a motor 29. Thus, the optical path of the optotype luminous flux reflected by the beam splitter 26 is shifted in an up or down direction to be adjusted to the positional height of the eye E, so that the optotype light is properly delivered to the eye E.

Numeral 30 is a detection optical system for detecting the positional height of the eye E. This optical system 30 includes a light condensing lens 31 and a two-dimensional position detecting element 32, which are disposed in the inside of the main unit 1 on right and left sides of the window 2. An infrared light emitted from a light-emitting section of the remote control unit 40 mentioned later is condensed by the condensing lens 31 onto the position detecting element 32 which outputs a detection signal. Based on this detection signal from the position detecting element 32, the height of the examinee's eye E is detected. The detail method of adjusting the optical path of the optotype luminous flux to the height of the examinee's eye is referred to U.S. Pat. No. 5,485,231 (corr. to Japanese Patent Unexamined Application No. 7-236612).

Next, the optotype disc plate 20 is explained in detail with reference to FIG. 4.

The optotypes such as Landolt rings and others to be used for the conventional visual acuity examination apparatuses are represented in decimal visual acuity values. As the optotypes to be used in the present embodiment, on the other hand, a visual angle of the minimum separation threshold is expressed in common logarithm (comparison optotypes expressed in geometrical series, which is hereinafter referred to as LogMAR (the logarithm of the minimum angle of resolution) optotype).

In the conventional decimal values for visual acuity, which are expressed as 0.1, 0.2–0.8, 0.9, 1.0 . . . , a visual acuity level changes by 0.1 each in decimal. Therefore, the improvement of visual acuity from 0.2 to 0.3 and the improvement from 0.9 to 1.0 are both regarded as one-level improvement of the visual acuity. In this conventional case, however, if expressing the visual acuity in terms of visual angle, the former corresponds to 1.5 times the visual angle, while the latter corresponds to 1.0/0.9=1.1 times. Consequently, it can not be said that the estimation of the visual acuity is accurately executed.

On the other hand, the LogMAR optotypes used in the present embodiment are formed in increments of 0.1 in a range of −0.3 to +1.4 on condition that the logarithmic visual acuity value of a Landolt ring optotype corresponding to decimal visual acuity value of 1.0 is regarded as zero. As a result of this, the size differences of optotypes according to visual acuity values are equal. On the other hand, the visual acuity values in the LogMAR optotypes are expressed as the decimal visual acuity values converted therefrom for the purpose of making them clearly understandable for examinees.

Figure 4:
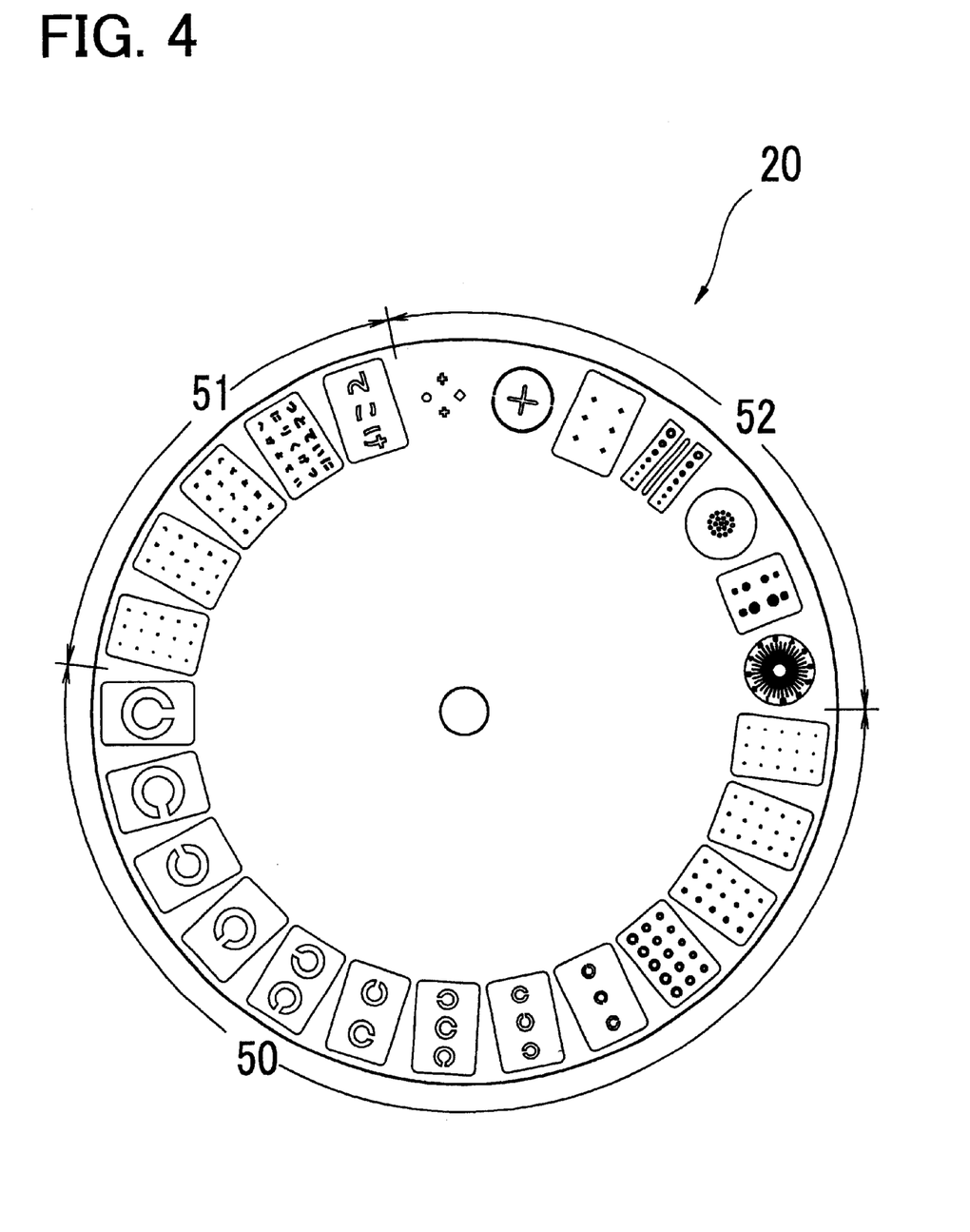
FIG. 4 is a front view of an optotype disc plate in the embodiment.

As shown in FIG. 4, the optotype disc plate 20 is provided thereon with a chart section 50 including thirteen charts each having Landolt ring optotypes in the LogMAR, a chart section 51 including five charts each having Hiragana character optotypes (which may be replaced by Alphabetical character optotypes) in the LogMAR, and a chart section 52 including seven charts to be used for a red and green test, a balance test of both eyes, and others. Thus, total twenty-four charts are formed on the disc plate 20 in a circle. A predetermined one of the above charts is placed on the optical path of the lamp 24 to be presented as a screen in the window 2.

Figure 6:
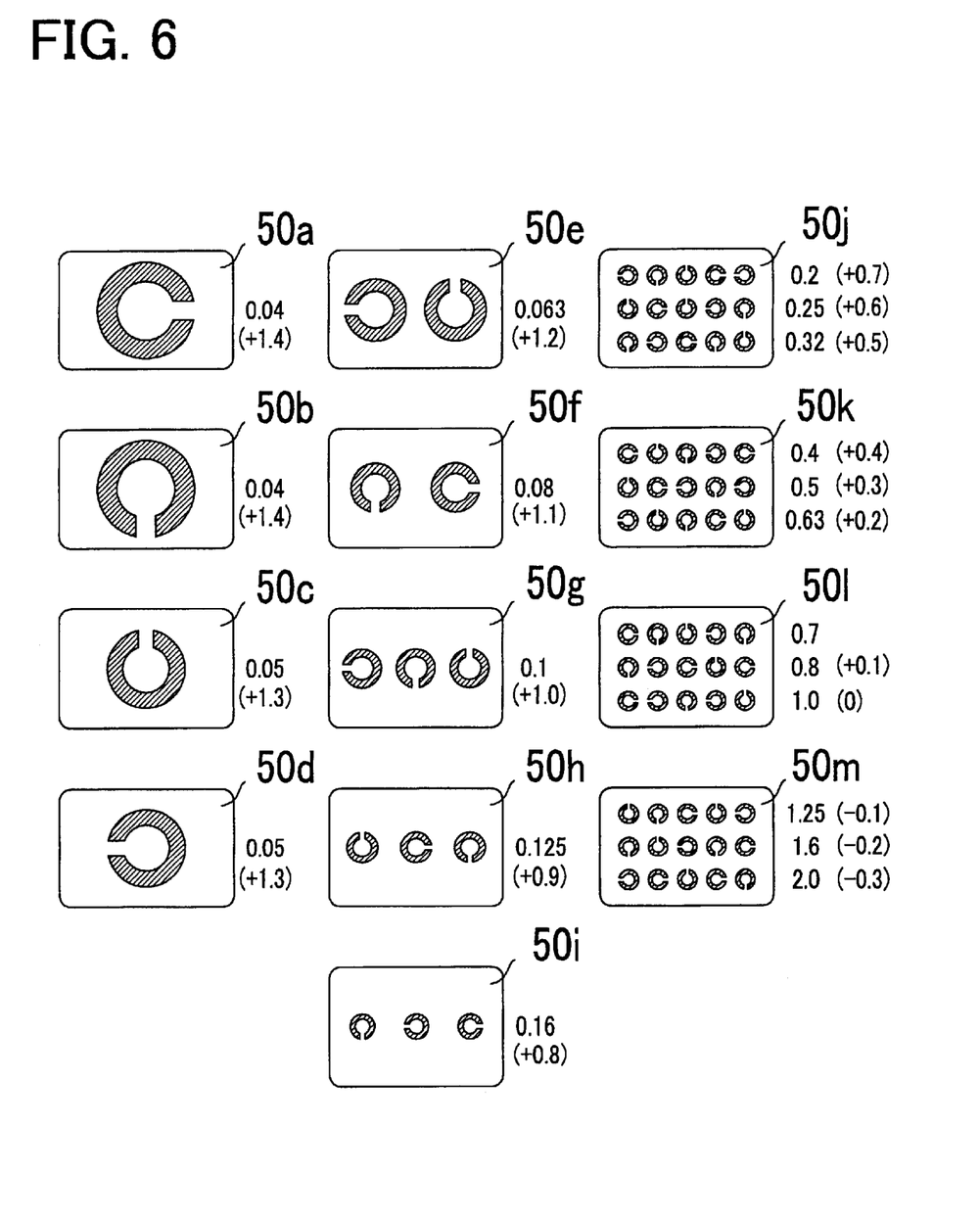
FIG. 6 is an explanatory view of charts on which Landolt ring optotypes are provided in the embodiment.

The chart section 50 is explained below in detail, referring to FIG. 6. In FIG. 6, small optotypes (Landolt ring optotypes for decimal visual acuity values of 0.25–2.0) are illustrated in enlarged sizes for convenience of explanation.

Charts 50a and 50b are each formed with a Landolt ring optotype for a decimal visual acuity value of 0.04 (a logarithmic visual acuity value of +1.4). Charts 50c and 50d are each formed with a Landolt ring optotype for a decimal visual acuity value of 0.05 (a logarithmic visual acuity value of +1.3). The Landolt ring optotypes formed on the charts 50a to 50d each have a slit formed in one direction selected from among four upper, lower, right, and left directions so that the slit directions are different from one another among the charts 50a–50d.

A chart 50e is formed with two Landolt ring optotypes for a decimal visual acuity value of 0.063 (a logarithmic visual acuity value of +1.2), which are laterally aligned. A chart 50f is formed with two Landolt ring optotypes for a decimal visual acuity value of 0.08 (a logarithmic visual acuity value of +1.1), which are laterally aligned as in the case of the chart 50e. The total four Landolt ring optotypes formed on the charts 50e and 50f each have a slit formed in one direction selected from among four upper, lower, right, and left directions so that the slit directions are different from one another among those four optotypes.

Charts 50g to 50i are each formed with three Landolt ring optotypes for a decimal visual acuity value of 0.1 (a logarithmic visual acuity value of +1.0), for 0.125 (+0.9), and for 0.16 (+0.8), respectively. The three Landolt ring optotypes in each chart are laterally aligned.

Charts 50j to 50m are each formed with Landolt ring optotypes for three kinds of visual acuity values, in which five Landolt ring optotypes are prepared for each visual acuity value. Each of the charts 50j to 50m therefore has total fifteen Landolt ring optotypes.

To be more specific, the chart 50j has three optotype groups for three decimal visual acuity values of 0.2, 0.25, and 0.32 (corresponding to logarithmic visual acuity values of +0.7, +0.6, and +0.5); the chart 50k has three optotype groups for decimal visual acuity values of 0.4, 0.5, and 0.63 (corr. to logarithmic visual acuity values of +0.4, +0.3, and +0.2); the chart 50l has three optotype groups for decimal visual acuity values of 0.7, 0.8, 1.0 (corr. to logarithmic visual acuity values of +0.1, 0); the chart 50m has three optotype groups for decimal visual acuity values of 1.25, 1.6, and 2.0 (corr. to logarithmic visual acuity values of −0.1, −0.2, and −0.3).

It is to be noted that the Landolt ring optotype for the decimal visual acuity value of 0.7 is not a LogMAR optotype shown in the present embodiment. However, the decimal visual acuity value of 0.7 is used as a reference visual acuity value for driver's licenses or the like, and therefore the optotype group for the decimal visual acuity value of 0.7 is added in the present embodiment.

In the chart section 51, five charts formed with Hiragana optotypes for decimal visual acuity values of 0.1 to 1.6 (corr. to logarithmic visual acuity values +1.0 to −0.2) are prepared. The optotype configuration in each of the charts is the same as that of the Landolt ring optotypes mentioned above, and its explanation is omitted.

Figure 5:
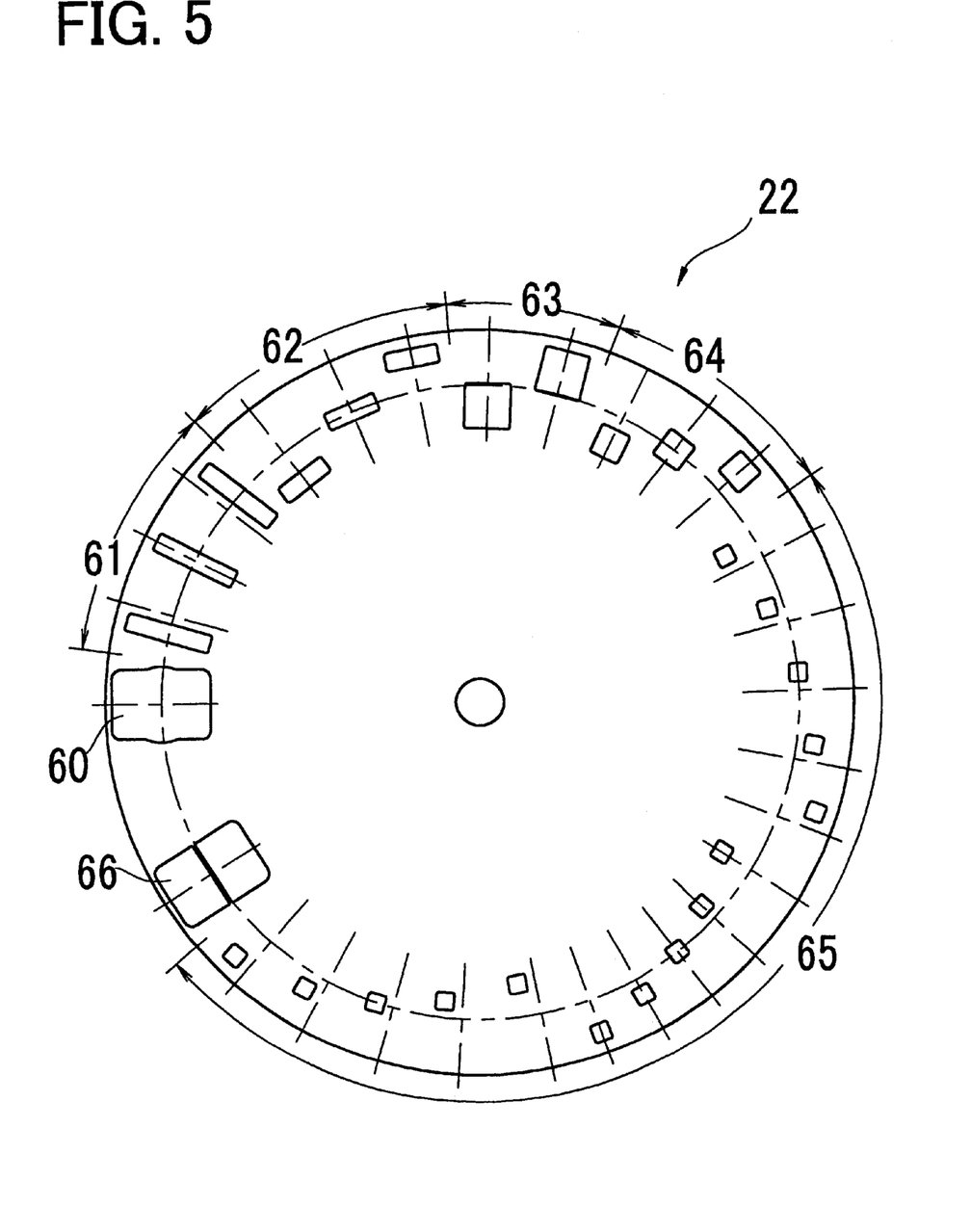
FIG. 5 is a front view of a mask disc plate in the embodiment.

Next, detailed explanation is made on the mask disc plate 22 for masking a desired portion of the optotype groups on the above charts, referring to FIG. 5. Dash-single-dot lines in the drawing correspond to centerlines of the charts in respective longitudinal and lateral directions.

Numeral 60 is an opening for allowing the entire face of a chart to be presented without masking. Numeral 61 denotes openings (lateral masks) for presenting the optotypes aligned in a lateral direction (corr. to a line in which the optotypes for the same visual acuity value are arranged) in each optotype group including three lines of five characters as shown in the charts 50j–50m, thereby separately presenting an upper, medium, and lower lines. Numeral 62 denotes openings (longitudinal masks) for presenting the optotypes aligned in a longitudinal direction (corr. to a column in which the optotypes for different visual acuity values are arranged) in the optotype group including three lines of five characters (five columns), thereby separately presenting a left, center, and right columns.

Numeral 63 denotes openings (single-character masks) for individually presenting the optotypes of the charts 50e and 50f in each of which the optotypes are formed in one line of two characters. Numeral 64 denotes openings (single-character masks) for individually presenting the optotypes of the charts 50g–50i and the like in each of which the optotypes are formed in one line of three characters. Numeral 65 denotes openings (single-character masks) for individually presenting the optotypes of the charts 50j–50m and the like in each of which the optotypes are formed in three lines of five characters.

Meanwhile, in the case where detailed estimation is made using the LogMAR optotypes as mentioned above, the kinds of optotypes for lower visual acuity values than a decimal visual acuity value of 0.2, that is, the kinds of large-sized optotypes, need to be increased. In order to examine an accurate visual acuity value, it is preferable to prepare different optotypes for the same visual acuity value (such as Landolt ring optotypes having different slit directions) in a larger number as much as possible. Accordingly, in the present embodiment, if one chart can have only one optotype due to its large size, at least two charts are prepared for providing two or more different optotypes for the same visual acuity value. If one chart can have plural optotypes for the same visual acuity value, each chart is formed with optotypes in the maximum number (with an upper limit of five optotypes in each line) with sufficient intervals between the adjacently arranged optotypes, thereby preventing interference with each other during the visual acuity examination.

To form different optotypes in a large number as much as possible in one chart with the increase of the optotypes for lower visual acuity, the kinds of configuration patterns of the optotype group formed on one chart should be increased. Therefore, without contrivance of the configuration patterns, many openings need to be formed on the mask disc plate 22 as compared with those in the conventional apparatus. That is, if one chart is provided with different optotypes in a large number as much as possible, the following configuration patterns are conceivable; for example, one line of one character, one line of two characters, two lines of three characters, three lines of five characters, and others. However, this needs many types of masks to apply single-character masks and lateral masks to all patterns, and therefore such the masks could not be formed in a single disc plate (mask disc).

In the present embodiment, as mentioned above, small-sized optotypes such as those in the charts 50j–50m are configured in three lines of five characters in one chart, while large-sized optotypes are configured in one line in one chart. Thus, even if many optotypes for lower visual acuity are formed in one chart, an optotype group in one lateral line per visual acuity value and one optotype can be presented in any of the charts, while the number of types of masks can be reduced to a minimum. This makes it possible to efficiently form masks in a single disc.

Figure 7:
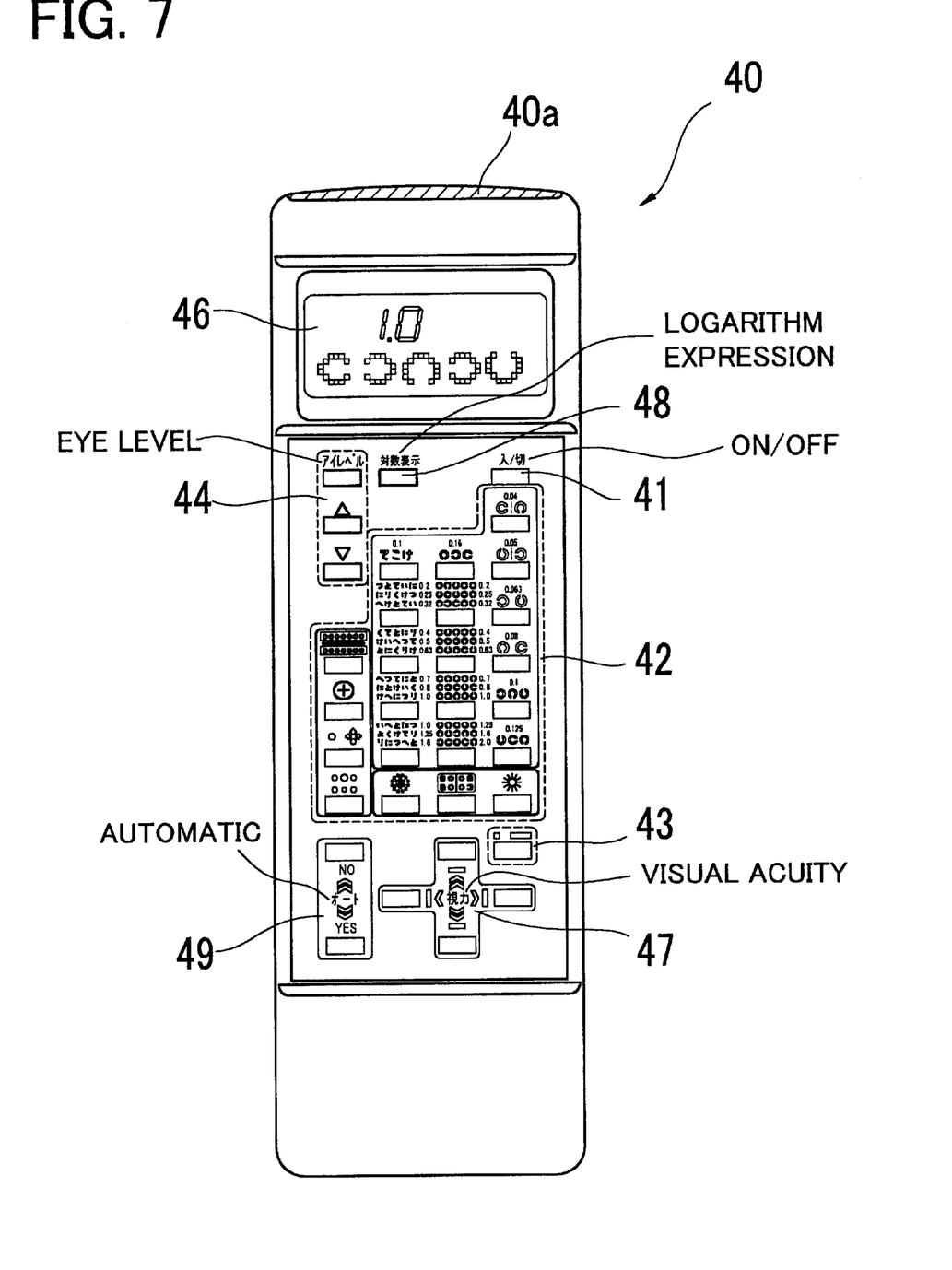
FIG. 7 is a front view of a remote control unit in the embodiment.

Next, the remote control unit 40 is described below in detail with reference to FIG. 7.

Numeral 41 denotes a power switch; 42 is a group of chart changing switches for selecting the chart; 43 is a mask switch for selecting the type of the mask to be applied to the optotypes; and 44 is a group of optical path changing switches for changing the direction of the optical path of an optotype presented to the examinee. This switch group 44 when operated transmits infrared light signals representative of positional detection for adjustment of the height of the examinee's eye E or the switch group 44 is used for manual operation to drive the motor 29, thereby changing the direction of the optical path. Numeral 46 is a display for displaying the optotype to be presented in the main unit 1 and its visual acuity value; 47 is a group of optotype changing switches for changing the optotypes to be presented by changing the position of the masks. Numeral 48 is a display changing switch for selecting the expression of the visual acuity value to be displayed in the display 46 between decimal and logarithm.

Numeral 49 is a group of automation switches for execution of a visual acuity examination program which will be mentioned later. This switch group 49 is also used for inputting whether the answer of the examinee about the optotype presented in the main unit 1 is right or wrong. The switch group 49 includes a YES switch to be used for the right answer of the examinee and a NO switch for the wrong answer or the case where the examinee answered he could not see or distinguish the presented optotype. The remote control unit 40 is also provided, at its front portion, with a signal transmittance/receipt portion 40a for transmitting/receiving pulse signals of infrared light.

Figure 8:
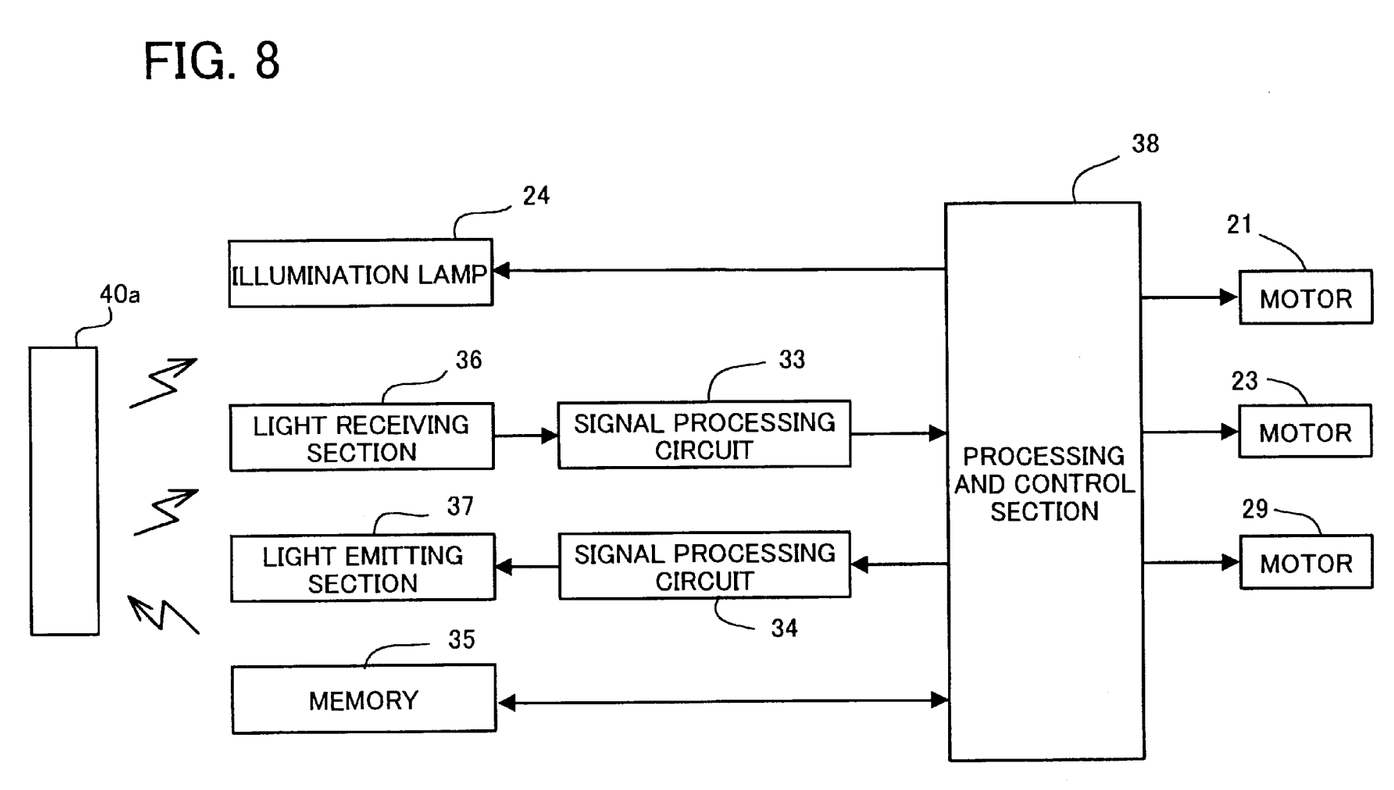
FIG. 8 is a block diagram of a control system (an electric system) of the apparatus in the embodiment.

Operation of the apparatus constructed as above will be explained below with reference to FIG. 8.

The examiner instructs, first, the examinee to take a predetermined position (which is at a distance of 0.9 m from the window 2 in the present embodiment) in front of the main unit 1. Then, the examiner manipulates the remote control unit 40 to start the visual acuity examination. The examiner operates the switch group 42, the switch 43, and the switch group 47 to present one or plural desired optotypes. The signal representative of the information on the selected optotypes and the mask, emitted from the signal transmittance/receipt portion 40a is received at a light receiving section 36 disposed in the main unit 1 through the signal transmittance/receipt window 4. The signal received at the light receiving section 36 is transmitted to a processing and control section 38 through a signal processing circuit 33. Upon receipt of the signal from the signal processing circuit 33, the processing and control section 38 causes the motors 21 and 23 to set the chart and the mask opening corresponding to the received signal onto the optical path. The processing and control section 38 then causes a light emitting section 37 to transmit a signal representative of the information on the presented optotype via a signal processing circuit 34. The transmitted signal is received at the signal transmission/receipt portion 40a of the remote control unit 40. The optotype information is displayed in the display 46 along with the visual acuity value, thereby to prevent inconsistency from occurring between the displayed optotype(s) and the presented optotype(s).

Next, explanation is made on an automatic examination for automatically presenting next optotypes by only input of a decision, right or wrong, with respect to the answer of the examinee by means of the switch group 49.

The examiner operates the switch group 42, the switch 43, and the switch group 47 to present an optotype regarded as being appropriate (distinguishable) for the examinee (this visual acuity value may be determined based on results of an objective examination and the like). The examiner asks the examinee to answer whether he can see (distinguish) or not the presented optotype, namely, a distinction result thereof. Confirming whether the answer of the examinee is right or wrong, the examiner presses the YES switch or NO switch of the switch group 49 in accordance with the confirmation result. Upon depression of the YES/NO switch, the automatic examination program mentioned below is executed. Furthermore, the information on the right or wrong answer, inputted with the switch group 49, is all recorded in a memory 35 and used for subsequent judgement routines and calculation of a final visual acuity value of the examinee.

The judgement routines of the automatic examination program in the present embodiment are explained below with reference to FIGS. 11, 12, and 13. Using those judgement routines, an example of a manner of determining a visual acuity value is explained with reference to FIG. 9. It is to be noted that the automatic examination program is stored in a storage circuit of the processing and control section 38.

Figure 9:
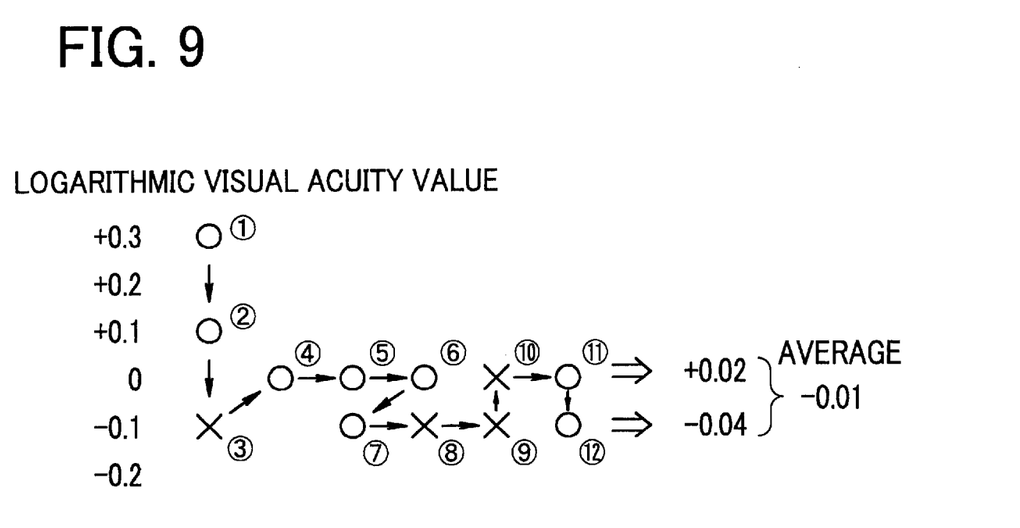
FIG. 9 is an explanatory view showing an example of a manner of determining a visual acuity value.

In FIG. 9, numerals (−0.2 to +0.3) written at the left are the logarithmic visual acuity values of the optotypes to be presented. A mark Ω denotes a right answer. A mark X denotes a wrong answer or the case where an examinee answered he could not distinguish a slit of a presented optotype. Circled numerals indicate the order of examination procedures.

If the answer of the examinee with respect to the optotype first presented (in the example shown in FIG. 9, the optotype for a logarithmic visual acuity value of +0.3 (corr. to a decimal visual acuity value of 0.5)) is right, in other words, if the YES switch is pressed, the estimation is made as follows in accordance with the judgement routine shown in FIG. 11 to decide the next optotype to be presented.

The processing and control section 38 confirms whether Log judgement is in progress (Step 1). The Log judgement in progress means the condition that, as a result of distinction made over several times, the maximum value among the visual acuity values (the smallest value for a logarithmic visual acuity value) at which the majority of examinee's answers about the optotypes for the same acuity value were right and the minimum value among the visual acuity values (the largest value for a logarithmic visual acuity value) at which the majority of examinee's answers about the optotypes for the same acuity value were wrong have already been obtained, and the next stage is only the distinction with respect to the unpresented optotypes for those two visual acuity values. In this example, since it is the first optotype distinction, the processing and control section 38 determines that the Log judgement is not in progress.

Successively, in Step 2, it is judged whether the visual acuity value has been decreased by two levels (to a logarithmic visual acuity value of +0.2). If NO in step 2, a decision is made as to whether there is no wrong answer in the examinations made until now (Step 3).

If there is no wrong answer, it is determined in Step 4 whether the currently presented optotype is an optotype for a visual acuity value higher by one-level (a logarithmic visual acuity value of +1.3) than the minimum visual acuity value, and then in Step 5 whether it is an optotype for the minimum visual acuity value (a logarithmic visual acuity value of +1.4). If NO in both Steps 4 and 5, in Step 6, the processing and control section 38 causes the optotype disc plate 20 and the mask disc plate 22 to rotate, thereby presenting an optotype for a visual acuity value higher by two-levels (a logarithmic visual acuity value of +0.1; a decimal visual acuity value of 0.8) to the examinee. If the answer of the examinee with respect to this optotype is right, the control section 38 controls, through the same steps as above, to present an optotype for a visual acuity value higher by another two-levels (a logarithmic visual acuity value of −0.1; a decimal visual acuity value of 1.25).

If the distinction answer with respect to the optotype for the logarithmic visual acuity value of −0.1 is wrong, the examiner depresses the NO switch. Upon depression of the NO switch, the next optotype to be presented is determined in accordance with the judgement routine shown in FIG. 12 (the judgement routine to be executed when the NO switch is depressed). Like in FIG. 11, after Step 1', it is determined in Step 2' whether the visual acuity value has been increased by two-levels (to a logarithmic visual acuity value of −0.2). In this example, since the visual acuity value has been increased by two-levels, the processing and control section 38 operates to present an optotype for a visual acuity value lower by one-level (to a logarithmic visual acuity value of 0; a decimal visual acuity value of 1.0) to the examinee in Step 7'.

Figure 11:
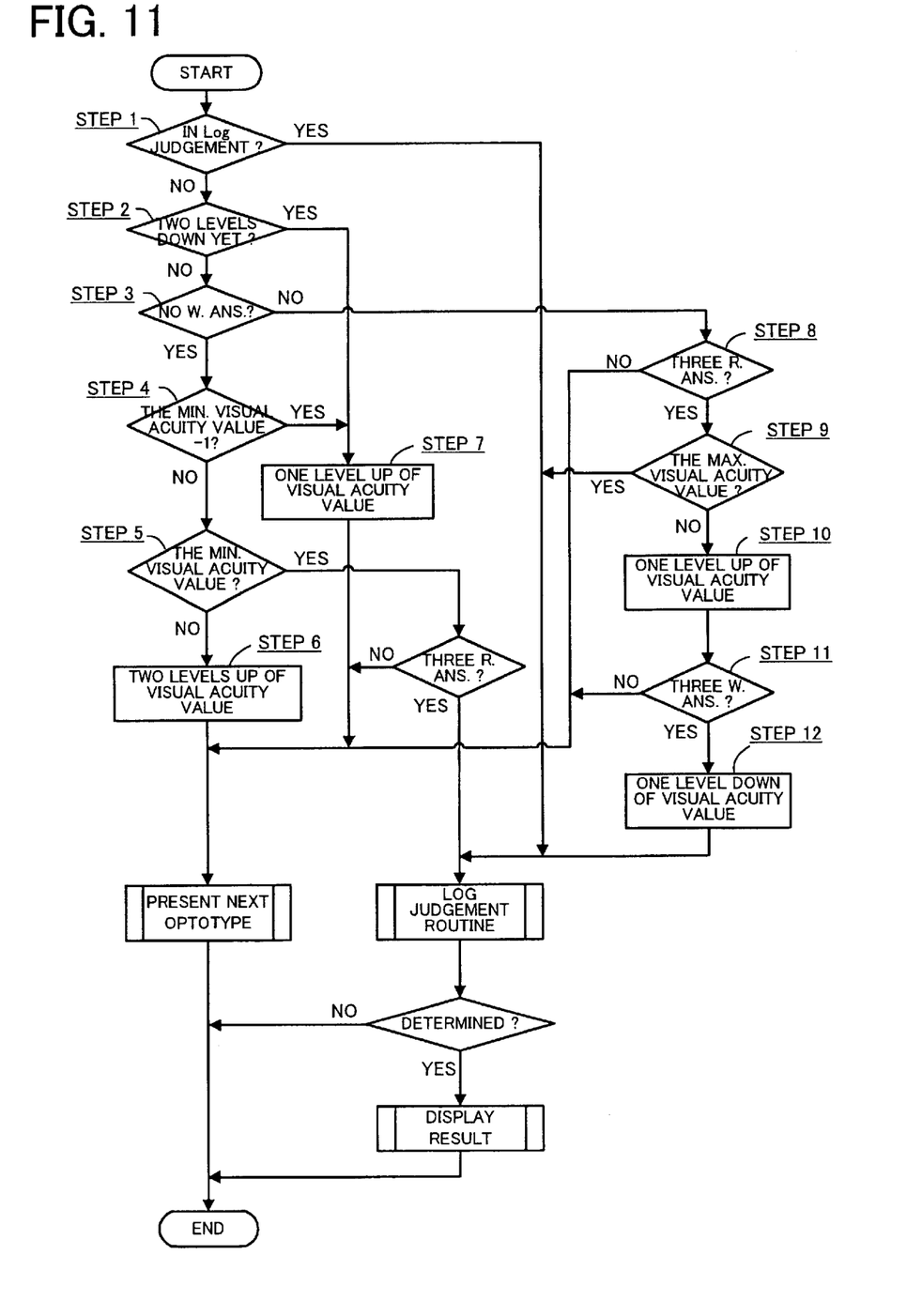
FIG. 11 is a flowchart of a judgment routine to be executed in response to depression of a YES switch.
Figure 12:
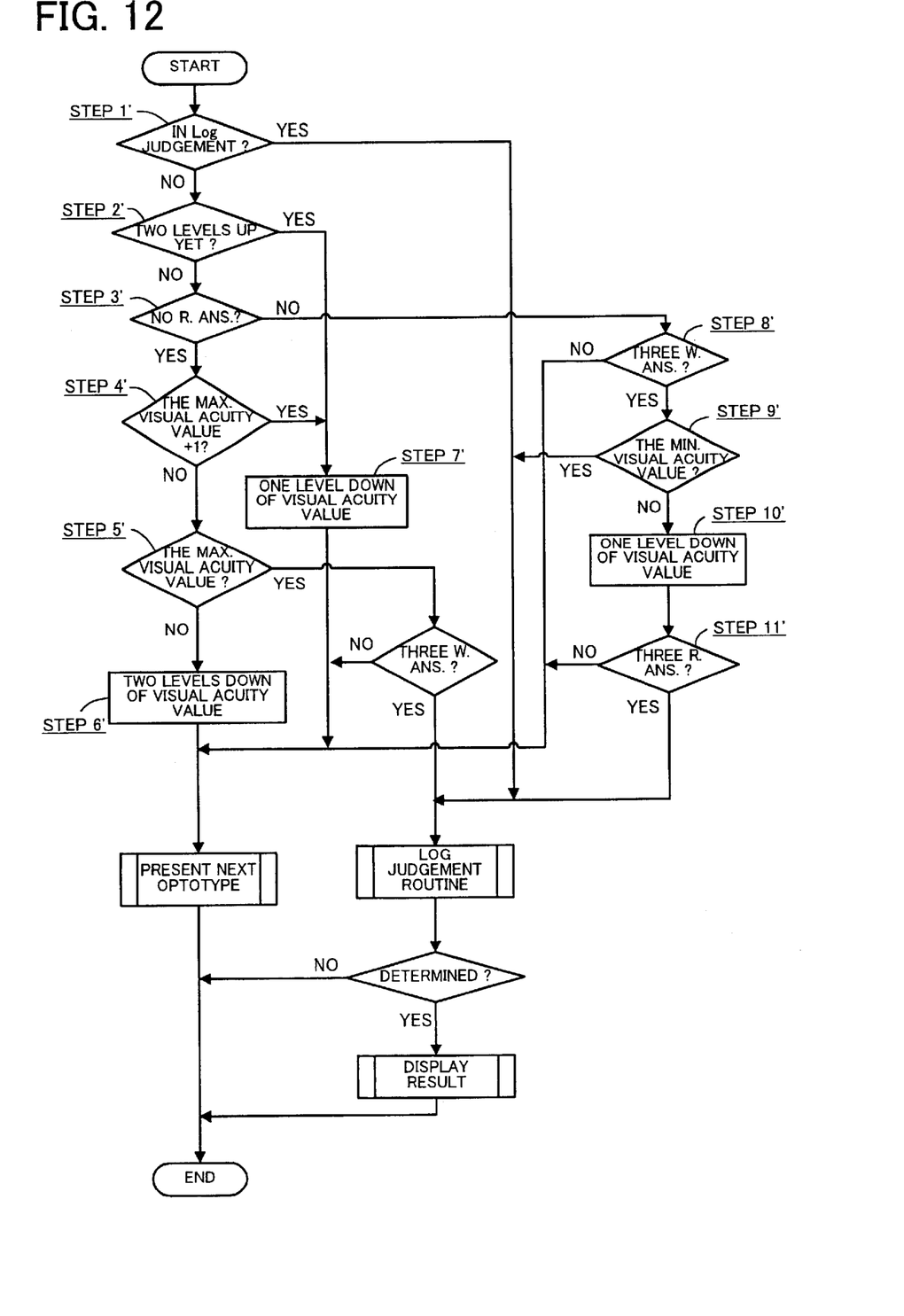
FIG. 12 is a flowchart of another judgment routine to be executed in response to depression of a NO switch.

If the distinction answer about the optotype for the logarithmic visual acuity value of 0 is right, a decision is made again in accordance with the judgement routine of FIG. 11. After Steps 1 and 2, the flow advances to Step 3. In this example, the distinction answer about the previously presented optotype for the logarithmic visual acuity value of −0.1 was wrong, and therefore it is determined in Step 8 whether there have been three right answers among the distinction answers about the optotypes for that visual acuity value. In this example, there are not three right answers and the processing and control section 38 presents a different optotype for the same visual acuity value (the logarithmic visual acuity value of 0).

In the above way, when the examinee distinguishes the optotypes for the logarithmic visual acuity value of 0 and gives right answers three times with respect to that visual acuity value, after Step 8, it is determined in Step 9 whether the optotypes are for the maximum visual acuity value (a logarithmic visual acuity value of −0.3). If it is not for the maximum visual acuity value, an optotype for a visual acuity value higher by one-level (a logarithmic visual acuity value of −0.1) in Step 10.

In Step 11, it is judged whether there have been three wrong answers among the distinction answers about the optotypes for the logarithmic visual acuity value of −0.1. If no three wrong answers, a different optotype from the previously presented optotypes is presented to the examinee. If the examinee gives a right answer with respect to the presented optotype, a different optotype for the same visual acuity value is presented in accordance with the judgment routine of FIG. 11. If the examinee gives a wrong answer with respect to the presented optotype, alternatively, a different optotype for the same visual acuity value is presented in accordance with the judgement routine of FIG. 12.

In the above manner, distinction is made several times with respect to the optotypes for the logarithmic visual acuity of −0.1. For the third wrong answer, the flow advances through Steps 1', 2', 3', 8', and 9' to Step 10' where an optotype for a lower visual acuity value by one-level (a logarithmic visual acuity value of 0) is presented. It is then determined whether there are three right answers (Step 1'). If YES, the Log judgement routine is executed from that visual acuity value.

Figure 13:
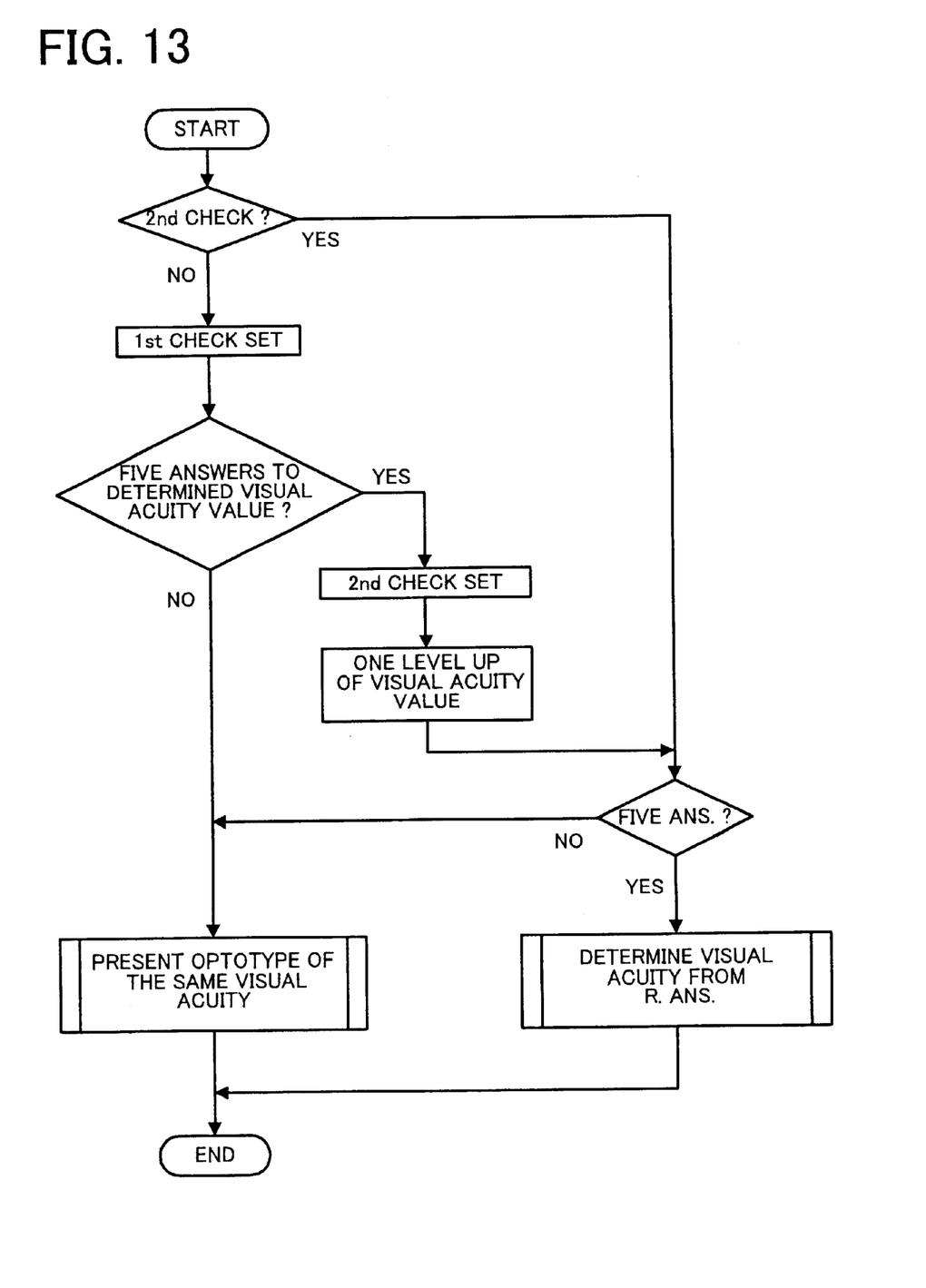
FIG. 13 is a flowchart of a Log judgment routine.

FIG. 13 shows a flowchart of the Log judgement routine. At this time, right answers have already been obtained about three optotypes which are the majority of five optotypes for the logarithmic visual acuity value of 0, and wrong answers have been obtained about three optotypes which are the majority of five optotypes for the logarithmic visual acuity value of −0.1. Thus, the subsequent optotype distinction is treated as the Log judgement in progress.

In this Log judgement routine, the unpresented optotypes (the remainder optotypes are two in this example) of the visual acuity value (the logarithmic visual acuity value of 0) at which three right answers have been obtained are presented in sequence. After all the optotypes (five in this example) are presented, the unpresented optotypes (the remainder is one in this example) for the visual acuity value (a visual acuity value higher by one-level (the logarithmic visual acuity value of −1)) at which three wrong answers have been obtained are presented in sequence to the examinee, allowing him to answer whether he can distinguish each of the optotypes.

When the distinction answers (right or wrong) are obtained about all the optotypes in relation to the two visual acuity values; the maximum value of the visual acuity values at which the three right answers have been obtained and the minimum value of the visual acuity values at which three wrong answers have been obtained, the processing and control section 38 determines the visual acuity value of the examinee based on the information on the right/wrong answers stored in the memory 35.

Processing of the visual acuity value in the present embodiment is performed in the following manner. In the case where there are five optotypes for the same visual acuity value, each optotype is assigned 0.02 each in logarithmic visual acuity value. If the answers about all the optotypes for the same visual acuity value are right, it is assumed that the same visual acuity value can be obtained. If there are wrong answers, on the other hand, 0.02 each in the logarithmic visual acuity value by the number of wrong answers is added to the visual acuity value. This is applied to the maximum value among the visual acuity values at which the examinee could distinguish and the minimum value among the visual acuity values at which the examinee could not distinguish. Thus, a further minute visual acuity value is found based on those two visual acuity values. Then, the two found visual acuity values are averaged to determine a final visual acuity value, which is treated as the visual acuity value of the examinee.

In the example shown in FIG. 9, at the logarithmic visual acuity value of 0 that is the maximum value of the visual acuity values at which the examinee could distinguish, there are four right answers and one wrong answer. Therefore, the minute visual acuity value at this level is $0+0.02\times1=0.02$. On the other hand, at the logarithmic visual acuity value of −0.1 that is the minimum value of the visual acuity value at which the examinee could not distinguish, there are two right answers and three wrong answers. As a result thereof, the minute visual acuity value at this level is $-0.1+0.02\times3=-0.04$. The two visual acuity values are averaged and a resultant final visual acuity value of the examinee is −0.01.

This result is displayed as the logarithmic in the display 46. If a corresponding decimal visual acuity value is desired, the switch 48 is depressed, whereby causing the processing and control section 38 to convert the logarithmic visual acuity value to the corresponding decimal visual acuity value, which is displayed on the display 46. In this example, this decimal visual acuity value displayed is 1.023.

As described above, in the present embodiment, the information on the right and wrong answers (a percentage of right answers) with respect to all the optotypes for the maximum value of the visual acuity values at which the examinee could distinguish and the information on the right and wrong answers with respect to all the optotypes for the minimum value of the visual acuity values at which the examinee could not distinguish are used to determine the visual acuity of the examinee. Consequently, the visual acuity examination apparatus in the present embodiment can provide a more accurate and minute visual acuity value as compared with the conventional estimation for a visual acuity value.

The present invention may be embodied in other specific forms without departing from the spirit or essential characteristics thereof. For instance, in the above embodiment, the right/wrong answers about three among five optotypes for the same visual acuity value are used to judge whether the examinee could distinguish that visual acuity value. Alternatively, based on whether the majority (or 60% or more) of answers about the optotypes for the same visual acuity value are right, it may be judged whether the examinee could distinguish the optotypes for that visual acuity value. For example, for four optotypes for the same visual acuity value, it may be determined that the examinee could distinguish the optotypes for that visual acuity value if only two or three among the answers are right. In this case, each of the optotypes is assigned 0.025 in the logarithmic visual acuity value. For only two optotypes for the same visual acuity value, it may be decided that the examinee could distinguish the optotypes for that visual acuity value only if all of the answers are right.

The examination procedure in the case where the next optotype is automatically presented in accordance with the answer of the examinee is not limited to the above. Any examination procedures may be adopted if only the maximum value among the visual acuity values at which the examinee could distinguish and the minimum value among the visual acuity values at which the examinee could not distinguish can be finally determined and the information on the right/wrong answers about all the optotypes for the two visual acuity values can be obtained.

Figure 10:
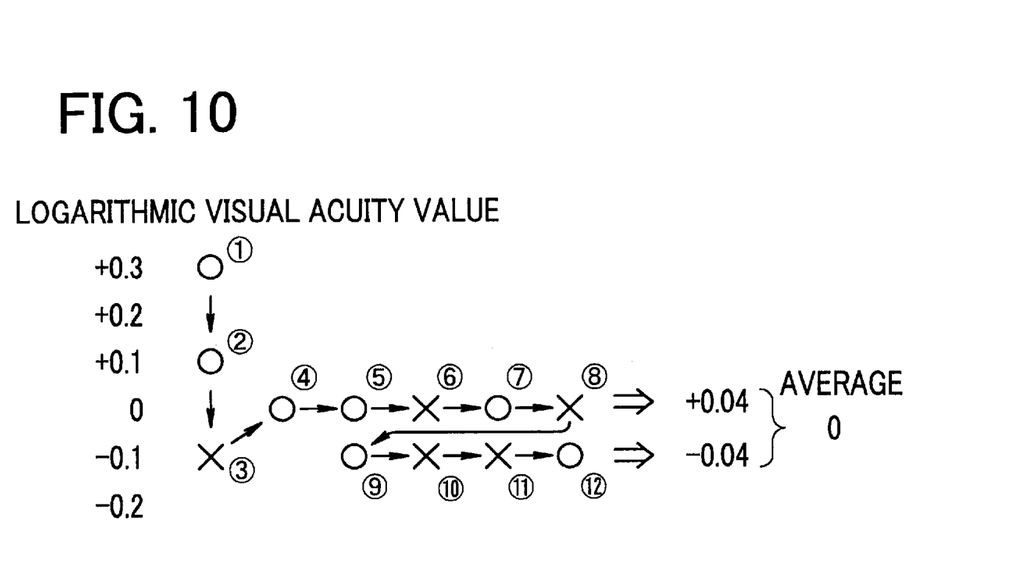
FIG. 10 is an explanatory view showing another example of a manner of determining a visual acuity value.

For instance, as shown in FIG. 10, the following procedure may be used; when the answer with respect to one optotype (e.g., an optotype for a logarithmic visual acuity value of −0.1) is wrong, the examinee is asked to individually distinguish all the optotypes for a visual acuity value lower by one-level (a logarithmic visual acuity value of 0) and then distinguish all the optotypes for the previous visual acuity value at which the examinee gave the wrong answer. In this case, if there are three wrong answers about the optotypes for the logarithmic visual acuity value of 0, the optotypes for a visual acuity value further lower by one-level (a logarithmic visual acuity value of +0.1) is presented and the same procedure is conducted.

In the above embodiment, the present invention is applied to the visual acuity examination apparatus capable of presenting optotypes in small space, but not limited thereto. The present invention may be applied to any visual acuity examination apparatuses capable of individually presenting optotypes under electrical control.

The answer results of the examinee may be input with a joystick or the like. In this case, the steps up to the right/wrong judgment with respect to the presented optotypes may be conducted in accordance with the automatic examination program, whereby more easily performing the examination.

According to the present invention, the visual acuity of the examinee's eye can accurately and easily be obtained and estimated.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A visual acuity examination apparatus for examining a visual acuity of an examinee by presenting an optotype to the examinee, the apparatus including:

an optotype presenting unit which selectively presents at least one of a plurality of comparison optotypes expressed in geometrical series, the optotypes being provided to be plural in number for each visual acuity value;

an input unit with which a distinction answer of the examinee with respect to the presented optotype is input;

a storage unit in which an examination program which sequentially determines an optotype to be next presented based on whether the distinction answer with respect to the presented optotype is right or wrong is stored;

a control unit which controls the optotype presenting unit in accordance with the examination program; and a processing unit which determines a visual acuity value of the examinee from a percentage of right answers in the distinction answers with respect to an optotype for a visual acuity value.

2. The visual acuity examination apparatus according to claim 1, wherein the examination program includes a step of sequentially presenting all of optotypes belonging to a first visual acuity value at which a majority of the distinction answers are right and all or some of optotypes belonging to a second visual acuity value which is higher by one level than the first visual acuity value, and the processing unit determines the visual acuity value from the percentages of right answers in relation to the first and second visual acuity values.

3. The visual acuity examination apparatus according to claim 2, wherein the presenting step included in the examination program includes a step of sequentially presenting all of the optotypes belonging to the first visual acuity value and then all of the optotypes belonging to the second visual acuity value.

4. The visual acuity examination apparatus according to claim 2, wherein the presenting step included in the examination program includes a step of sequentially presenting the optotypes belonging to the second visual acuity value when the majority of the distinction answers in relation to the first visual acuity value are right, and sequentially presenting unpresented optotypes belonging to the first visual acuity value again when the majority of the distinction answers in relation to the second visual acuity value are wrong.

5. The visual acuity examination apparatus according to claim 1 further including a display unit which displays the visual acuity value determined by the processing unit, the visual acuity value being expressed in a form selected between a logarithmic visual acuity value form and a decimal visual acuity value form.

6. The visual acuity examination apparatus according to claim 1, wherein the optotype presenting unit includes:
- an optotype disc plate on which a plurality of charts each provided with one optotype or a plurality of optotypes is formed in a circle;
- a mask disc plate on which a plurality of masks for presenting one optotype or at least a part of the optotypes formed on the chart;
- a rotating unit which individually rotates the optotype disc plate and the mask disc plate, thereby to selectively present the optotype; and
the control unit controls the rotating unit in accordance with the examination program.

7. The visual acuity examination apparatus according to claim 6, wherein the plurality of optotypes formed on the chart are configured in one line or three lines.

8. The visual acuity examination apparatus according to claim 7, wherein the optotypes each having a small size corresponding to decimal visual acuity values of 0.2 or less are configured in three lines of five characters, while the optotypes each having a large size corresponding to visual acuity values of more than 0.2 are configured in one line.

9. The visual acuity examination apparatus according to claim 7, wherein the plurality of masks include a single-character mask for individually presenting the one optotype and a lateral mask for presenting the optotypes per line among the optotypes configured in three lines.

10. A visual acuity examination apparatus for examining a visual acuity of an examinee by presenting an optotype to the examinee, the apparatus including:
- an optotype presenting unit which selectively presents at least one of a plurality of comparison optotypes expressed in geometrical series, the optotypes being provided to be plural in number for each visual acuity value;
- an input unit with which a distinction answer of the examinee with respect to the presented optotype is input;
- a storage unit in which an examination program which sequentially determines an optotype to be next presented based on whether the distinction answer with respect to the presented optotype is right or wrong is stored;
- a control unit which controls the optotype presenting unit in accordance with the examination program;
- a processing unit which determines a visual acuity value of the examinee from a result of distinction answers with respect to an optotype for a visual acuity value; and
- a display unit which displays the visual acuity value determined by the processing unit, the visual acuity value being expressed in a form selected between a logarithmic visual acuity value form and a decimal visual acuity value form.

* * * * *